(12) United States Patent
Kostrzewski

(10) Patent No.: US 8,308,041 B2
(45) Date of Patent: Nov. 13, 2012

(54) STAPLE FORMED OVER THE WIRE WOUND CLOSURE PROCEDURE

(75) Inventor: Stanislaw Kostrzewski, Newtown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 38 days.

(21) Appl. No.: 12/943,221

(22) Filed: Nov. 10, 2010

(65) Prior Publication Data

US 2012/0111920 A1    May 10, 2012

(51) Int. Cl.
*A61B 17/068* (2006.01)
(52) U.S. Cl. .................. 227/175.1; 227/19; 227/176.1; 606/139; 606/219
(58) Field of Classification Search ............... 227/19, 227/175.1, 176.1, 180.1; 606/139, 143, 151, 606/153, 219
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,244,372 A | 1/1981 | Kapitanov et al. | |
| 4,345,600 A * | 8/1982 | Rothfuss | 606/148 |
| 4,429,695 A | 2/1984 | Green | |
| 4,496,090 A | 1/1985 | Crevier et al. | |
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,749,114 A * | 6/1988 | Green | 227/19 |
| 4,752,024 A | 6/1988 | Green et al. | |
| 4,784,137 A | 11/1988 | Kulik et al. | |

(Continued)

FOREIGN PATENT DOCUMENTS

AU    5476586    9/1986

(Continued)

*Primary Examiner* — Scott A. Smith

(57) ABSTRACT

An anvil assembly is provided and includes an anvil member having a plurality of staple bending pockets formed in a face of the anvil member and a length of reinforcing material suspended across the staple bending pockets. Longitudinal channels are provided in the face of the anvil member to releasably retain the reinforcing material. The longitudinal channels transect the staple bending pockets and support and suspend the reinforcing material over the staple bending pockets such that a leg of a surgical staple can be bent around the reinforcing material. Various configurations of fully formed staples are also disclosed and include a backspan having first and second legs extending from the backspan. First portions of each of the first and legs extend from the backspan and define a plane with the backspan. Second portions of each of the first and second legs extend from the first portions and project outwardly from the plane defined by the backspan and the first second portions.

22 Claims, 10 Drawing Sheets

U.S. PATENT DOCUMENTS

| | | |
|---|---|---|
| 4,821,939 A * | 4/1989 | Green .............................. 227/19 |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,368,599 A * | 11/1994 | Hirsch et al. ................... 606/139 |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,571,117 A * | 11/1996 | Ahn .............................. 606/139 |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,649,938 A * | 7/1997 | Allen et al. ................... 606/144 |
| 5,651,491 A | 7/1997 | Heaton et al. |
| 5,653,373 A | 8/1997 | Green et al. |
| 5,653,374 A | 8/1997 | Young et al. |

| | | | | | | |
|---|---|---|---|---|---|---|
| 5,653,721 | A | 8/1997 | Knodel et al. | 5,919,198 A | 7/1999 | Graves, Jr. et al. |
| 5,655,698 | A | 8/1997 | Yoon | 5,922,001 A | 7/1999 | Yoon |
| 5,657,921 | A | 8/1997 | Young et al. | 5,931,847 A | 8/1999 | Bittner et al. |
| 5,658,300 | A | 8/1997 | Bito et al. | 5,941,442 A | 8/1999 | Geiste et al. |
| 5,662,258 | A | 9/1997 | Knodel et al. | 5,954,259 A | 9/1999 | Viola et al. |
| 5,662,259 | A | 9/1997 | Yoon | 5,964,774 A | 10/1999 | McKean et al. |
| 5,662,260 | A | 9/1997 | Yoon | 5,980,510 A | 11/1999 | Tsonton et al. |
| 5,662,662 | A | 9/1997 | Bishop et al. | 5,988,479 A | 11/1999 | Palmer |
| 5,662,666 | A | 9/1997 | Onuki et al. | 6,004,335 A | 12/1999 | Vaitekunas et al. |
| 5,665,085 | A | 9/1997 | Nardella | 6,010,054 A | 1/2000 | Johnson et al. |
| 5,667,517 | A | 9/1997 | Hooven | 6,032,849 A | 3/2000 | Mastri et al. |
| 5,669,544 | A | 9/1997 | Schulze et al. | 6,045,560 A | 4/2000 | McKean et al. |
| 5,673,840 | A | 10/1997 | Schulze et al. | 6,063,097 A | 5/2000 | Oi et al. |
| 5,673,841 | A | 10/1997 | Schulze et al. | 6,079,606 A | 6/2000 | Milliman et al. |
| 5,673,842 | A | 10/1997 | Bittner et al. | 6,099,551 A | 8/2000 | Gabbay |
| 5,676,674 | A | 10/1997 | Bolanos et al. | 6,109,500 A | 8/2000 | Alli et al. |
| 5,680,981 | A | 10/1997 | Mililli et al. | 6,131,789 A | 10/2000 | Schulze et al. |
| 5,680,982 | A | 10/1997 | Schulze et al. | 6,131,790 A | 10/2000 | Piraka |
| 5,680,983 | A | 10/1997 | Plyley et al. | 6,155,473 A | 12/2000 | Tompkins et al. |
| 5,690,269 | A | 11/1997 | Bolanos et al. | 6,197,017 B1 | 3/2001 | Brock et al. |
| 5,692,668 | A | 12/1997 | Schulze et al. | 6,202,914 B1 | 3/2001 | Geiste et al. |
| 5,697,542 | A | 12/1997 | Knodel et al. | 6,241,139 B1 | 6/2001 | Milliman et al. |
| 5,702,409 | A | 12/1997 | Rayburn et al. | 6,250,532 B1 | 6/2001 | Green et al. |
| 5,704,534 | A | 1/1998 | Huitema et al. | 6,264,086 B1 | 7/2001 | McGuckin, Jr. |
| 5,706,997 | A | 1/1998 | Green et al. | 6,264,087 B1 | 7/2001 | Whitman |
| 5,709,334 | A | 1/1998 | Sorrentino et al. | 6,269,977 B1 | 8/2001 | Moore |
| 5,711,472 | A | 1/1998 | Bryan | 6,279,809 B1 | 8/2001 | Nicolo |
| 5,713,505 | A | 2/1998 | Huitema | 6,315,183 B1 | 11/2001 | Piraka |
| 5,715,988 | A | 2/1998 | Palmer | 6,315,184 B1 | 11/2001 | Whitman |
| 5,716,366 | A | 2/1998 | Yates | 6,325,810 B1 | 12/2001 | Hamilton et al. |
| 5,718,359 | A | 2/1998 | Palmer | 6,330,965 B1 | 12/2001 | Milliman et al. |
| 5,725,536 | A | 3/1998 | Oberlin et al. | 6,391,038 B2 | 5/2002 | Vargas et al. |
| 5,725,554 | A | 3/1998 | Simon et al. | 6,398,797 B2 | 6/2002 | Bombard et al. |
| 5,728,110 | A | 3/1998 | Vidal et al. | 6,436,097 B1 | 8/2002 | Nardella |
| 5,732,806 | A | 3/1998 | Foshee et al. | 6,439,446 B1 | 8/2002 | Perry et al. |
| 5,735,848 | A | 4/1998 | Yates et al. | 6,443,973 B1 | 9/2002 | Whitman |
| 5,743,456 | A | 4/1998 | Jones et al. | 6,463,623 B2 | 10/2002 | Ahn et al. |
| 5,749,893 | A | 5/1998 | Vidal et al. | 6,478,804 B2 | 11/2002 | Vargas et al. |
| 5,752,644 | A | 5/1998 | Bolanos et al. | 6,488,196 B1 | 12/2002 | Fenton, Jr. |
| 5,762,255 | A | 6/1998 | Chrisman et al. | 6,503,257 B2 | 1/2003 | Grant et al. |
| 5,762,256 | A | 6/1998 | Mastri et al. | 6,505,768 B2 | 1/2003 | Whitman |
| 5,769,303 | A | 6/1998 | Knodel et al. | 6,544,274 B2 | 4/2003 | Danitz et al. |
| 5,769,892 | A | 6/1998 | Kingwell | 6,554,844 B2 | 4/2003 | Lee et al. |
| 5,772,099 | A | 6/1998 | Gravener | 6,565,554 B1 | 5/2003 | Niemeyer |
| 5,772,673 | A | 6/1998 | Cuny et al. | 6,587,750 B2 | 7/2003 | Gerbi et al. |
| 5,779,130 | A | 7/1998 | Alesi et al. | 6,592,597 B2 | 7/2003 | Grant et al. |
| 5,779,131 | A | 7/1998 | Knodel et al. | 6,594,552 B1 | 7/2003 | Nowlin et al. |
| 5,779,132 | A | 7/1998 | Knodel et al. | 6,602,252 B2 | 8/2003 | Mollenauer |
| 5,782,396 | A | 7/1998 | Mastri et al. | 6,612,053 B2 | 9/2003 | Liao |
| 5,782,397 | A | 7/1998 | Koukline | 6,619,529 B2 | 9/2003 | Green et al. |
| 5,782,834 | A | 7/1998 | Lucey et al. | D480,808 S | 10/2003 | Wells et al. |
| 5,785,232 | A | 7/1998 | Vidal et al. | 6,644,532 B2 | 11/2003 | Green et al. |
| 5,797,536 | A | 8/1998 | Smith et al. | 6,656,193 B2 | 12/2003 | Grant et al. |
| 5,797,537 | A | 8/1998 | Oberlin et al. | 6,669,073 B2 | 12/2003 | Milliman et al. |
| 5,797,538 | A | 8/1998 | Heaton et al. | 6,681,978 B2 | 1/2004 | Geiste et al. |
| 5,810,811 | A | 9/1998 | Yates et al. | 6,698,643 B2 | 3/2004 | Whitman |
| 5,810,855 | A | 9/1998 | Rayburn et al. | 6,716,232 B1 | 4/2004 | Vidal et al. |
| 5,814,055 | A | 9/1998 | Knodel et al. | 6,722,552 B2 | 4/2004 | Fenton, Jr. |
| 5,814,057 | A | 9/1998 | Oi et al. | 6,731,473 B2 | 5/2004 | Li et al. |
| 5,816,471 | A | 10/1998 | Plyley et al. | 6,755,338 B2 | 6/2004 | Hahnen et al. |
| 5,817,109 | A | 10/1998 | McGarry et al. | 6,783,524 B2 | 8/2004 | Anderson et al. |
| 5,820,009 | A | 10/1998 | Melling et al. | 6,786,382 B1 | 9/2004 | Hoffman |
| 5,823,066 | A | 10/1998 | Huitema et al. | 6,808,262 B2 | 10/2004 | Chapoy et al. |
| 5,826,776 | A | 10/1998 | Schulze et al. | 6,817,509 B2 | 11/2004 | Geiste et al. |
| 5,829,662 | A | 11/1998 | Allen et al. | 6,830,174 B2 | 12/2004 | Hillstead et al. |
| 5,833,695 | A | 11/1998 | Yoon | 6,835,199 B2 | 12/2004 | McGuckin, Jr. et al. |
| 5,836,147 | A | 11/1998 | Schnipke | 6,843,403 B2 | 1/2005 | Whitman |
| 5,862,972 | A | 1/1999 | Green et al. | RE38,708 E | 3/2005 | Bolanos et al. |
| 5,865,361 | A | 2/1999 | Milliman et al. | 6,877,647 B2 | 4/2005 | Green et al. |
| 5,871,135 | A | 2/1999 | Williamson, IV et al. | 6,879,880 B2 | 4/2005 | Nowlin et al. |
| 5,873,873 | A | 2/1999 | Smith et al. | 6,889,116 B2 | 5/2005 | Jinno |
| 5,878,938 | A | 3/1999 | Bittner et al. | 6,905,057 B2 | 6/2005 | Swayze et al. |
| 5,893,506 | A | 4/1999 | Powell | 6,953,138 B1 | 10/2005 | Dworak et al. |
| 5,894,979 | A | 4/1999 | Powell | 6,953,139 B2 | 10/2005 | Milliman et al. |
| 5,897,562 | A | 4/1999 | Bolanos et al. | 6,959,852 B2 | 11/2005 | Shelton, IV et al. |
| 5,901,895 | A | 5/1999 | Heaton et al. | 6,962,594 B1 | 11/2005 | Thevenet |
| 5,911,352 | A | 6/1999 | Racenet et al. | 6,964,363 B2 | 11/2005 | Wales et al. |
| 5,911,353 | A | 6/1999 | Bolanos et al. | 6,978,921 B2 | 12/2005 | Shelton, IV et al. |
| 5,918,791 | A | 7/1999 | Sorrentino et al. | 6,979,338 B1 * | 12/2005 | Loshakove et al. ........... 606/153 |

| | | |
|---|---|---|
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielson et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |

| Patent/Publication | Date | Name |
|---|---|---|
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,721,933 B2 | 5/2010 | Ehrenfels et al. |
| 7,726,538 B2 | 6/2010 | Holsten et al. |
| 7,726,539 B2 | 6/2010 | Holsten et al. |
| 7,740,160 B2 | 6/2010 | Viola |
| 7,744,628 B2 | 6/2010 | Viola |
| 7,762,445 B2 | 7/2010 | Heinrich et al. |
| 7,951,166 B2 * | 5/2011 | Orban et al. .................. 606/215 |
| 7,959,053 B2 * | 6/2011 | Yasuda ...................... 227/180.1 |
| 2004/0007608 A1 | 1/2004 | Ehrenfels et al. |
| 2004/0050902 A1 | 3/2004 | Green et al. |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet |
| 2005/0119669 A1 | 6/2005 | Demmy |
| 2005/0127131 A1 | 6/2005 | Mastri |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0043147 A1 | 3/2006 | Mastri et al. |
| 2006/0049229 A1 | 3/2006 | Milliman et al. |
| 2006/0049230 A1 | 3/2006 | Shelton, IV et al. |
| 2006/0060630 A1 | 3/2006 | Shelton, IV et al. |
| 2006/0081678 A1 | 4/2006 | Ehrenfels et al. |
| 2006/0097026 A1 | 5/2006 | Shelton, IV |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton, IV |
| 2007/0045380 A1 | 3/2007 | Mastri et al. |
| 2007/0068989 A1 | 3/2007 | Shelton, IV |
| 2007/0068990 A1 | 3/2007 | Shelton, IV et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton, IV et al. |
| 2007/0084896 A1 | 4/2007 | Doll et al. |
| 2007/0084897 A1 | 4/2007 | Shelton, IV et al. |
| 2007/0084898 A1 | 4/2007 | Scirica |
| 2007/0084899 A1 | 4/2007 | Taylor |
| 2007/0102472 A1 | 5/2007 | Shelton, IV |
| 2007/0102473 A1 | 5/2007 | Shelton, IV |
| 2007/0102474 A1 | 5/2007 | Shelton, IV |
| 2007/0102475 A1 | 5/2007 | Ortiz et al. |
| 2007/0102476 A1 | 5/2007 | Shelton, IV |
| 2007/0106317 A1 | 5/2007 | Shelton, IV |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton, IV |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton, IV et al. |
| 2007/0175947 A1 | 8/2007 | Ortiz et al. |
| 2007/0175948 A1 | 8/2007 | Scirica et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175954 A1 | 8/2007 | Viola |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179528 A1 | 8/2007 | Soltz et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |

| | | |
|---|---|---|
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffen et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0006620 A1 | 1/2010 | Sorrentino et al. |
| 2010/0012702 A1 | 1/2010 | Marczyk |
| 2010/0012703 A1 | 1/2010 | Calabrese et al. |
| 2010/0012704 A1 | 1/2010 | Racenet et al. |
| 2010/0025452 A1 | 2/2010 | Whitman |
| 2010/0032470 A1 | 2/2010 | Hess et al. |
| 2010/0044411 A1 | 2/2010 | Viola |
| 2010/0065605 A1 | 3/2010 | Shelton et al. |
| 2010/0065606 A1 | 3/2010 | Stopek et al. |
| 2010/0065608 A1 | 3/2010 | Olson et al. |
| 2010/0069942 A1 | 3/2010 | Shelton, IV et al. |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072258 A1 | 3/2010 | Farascioni et al. |
| 2010/0076429 A1 | 3/2010 | Heinrich |
| 2010/0076459 A1 | 3/2010 | Farascioni |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |

| | | | | | | |
|---|---|---|---|---|---|---|
| EP | 0213817 | 11/1987 | | EP | 0621006 | 10/1994 |
| EP | 0273468 | 7/1988 | | EP | 0621009 | 10/1994 |
| EP | 0324166 | 7/1989 | | EP | 0656188 | 6/1995 |
| EP | 0324635 | 7/1989 | | EP | 0365153 | 8/1995 |
| EP | 0324637 | 7/1989 | | EP | 0666057 | 8/1995 |
| EP | 0324638 | 7/1989 | | EP | 0705571 | 4/1996 |
| EP | 0369324 | 5/1990 | | EP | 0760230 | 3/1997 |
| EP | 0373762 | 6/1990 | | FR | 2542188 | 9/1984 |
| EP | 0380025 | 8/1990 | | FR | 2660851 | 10/1991 |
| EP | 0399701 | 11/1990 | | FR | 2681775 | 10/1991 |
| EP | 0449394 | 10/1991 | | GB | 1352554 | 4/1971 |
| EP | 0484677 | 5/1992 | | GB | 1452185 | 10/1976 |
| EP | 0489436 | 6/1992 | | GB | 1555455 | 11/1979 |
| EP | 0503662 | 9/1992 | | GB | 2048685 | 12/1980 |
| EP | 0514139 | 11/1992 | | GB | 2070499 | 9/1981 |
| EP | 0536903 | 4/1993 | | GB | 2141066 | 12/1984 |
| EP | 0537572 | 4/1993 | | GB | 2165559 | 4/1986 |
| EP | 0539762 | 5/1993 | | JP | Sho 51-149985 | 12/1976 |
| EP | 0545029 | 6/1993 | | SU | 659146 | 4/1979 |
| EP | 0552050 | 7/1993 | | SU | 728848 | 5/1980 |
| EP | 0552423 | 7/1993 | | SU | 980703 | 12/1982 |
| EP | 0579038 | 1/1994 | | SU | 990220 | 1/1983 |
| EP | 0589306 | 3/1994 | | WO | WO8302247 | 7/1983 |
| EP | 0591946 | 4/1994 | | WO | WO 89/10094 | 11/1989 |
| EP | 0592243 | 4/1994 | | WO | WO9210976 | 7/1992 |
| EP | 0593920 | 4/1994 | | WO | 9308754 | 5/1993 |
| EP | 0598202 | 5/1994 | | WO | 9314706 | 8/1993 |
| EP | 0598579 | 5/1994 | | | | |

* cited by examiner

STAPLE FORMED OVER THE WIRE WOUND CLOSURE PROCEDURE

BACKGROUND

1. Technical Field

The present disclosure relates to a surgical instrument and method of forming a staple over a structural component to clamp tissue during a wound closure procedure. More particularly, the present disclosure relates to an anvil assembly incorporating a clamping wire and staple pockets configured to form tissue penetrating ends of a staple about the clamping wire to secure tissues during a wound closure procedure.

2. Background of Related Art

Surgical stapling devices are employed by surgeons to sequentially or simultaneously apply one or more rows of fasteners, e.g., staples or two-part fasteners, to body tissue for the purpose of joining segments of body tissue together. Such devices generally consist of a pair of jaws or finger-like structures between which the body tissue to be joined is placed. When the stapling device is actuated, or "fired", longitudinally moving firing bars contact staple drive members in one of the jaws. The staple drive members push the surgical staples through the body tissue and into an anvil in the opposite jaw which crimps the staples closed. If tissue is to be removed or separated, a knife blade can be provided in the jaws of the device to cut the tissue between the lines of staples.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a reinforcing or "buttress" material between the backspan of the staple and the underlying tissue. In this method, a layer of buttress material is placed against the tissue and the tissue is stapled in conventional manner. In more recent methods, the buttress material is positioned on the stapling instrument itself prior to stapling the tissue. An example of this is disclosed in U.S. Pat. No. 5,542,594 to McKean et al. In McKean et al. a tube of buttress material is slipped over the jaw of the stapler. The stapler is then actuated to staple the subject tissue and secure the buttress material between the tissue and staple line to reinforce the tissue and staple line.

Thus, it would be desirable to provide a system of attaching localized reinforcing material to an anvil of a surgical stapling instrument. It would be further desirable to provide a system of attaching a limited amount of buttress material to either side of a knife groove formed in an anvil of a surgical stapling instrument such that the material is localized on either side of the staple line to avoid having to cut the reinforcing material. It would be still further desirable to provide an anvil having staple clinching pockets configured to bend tissue penetrating ends of a surgical staple over the reinforcing material and back into the tissues to further secure the reinforcing material to the tissues and without penetrating the reinforcing material.

SUMMARY

There is disclosed an anvil assembly, for use with a surgical stapling instrument, which generally includes an anvil member having a longitudinal axis and a first staple bending pocket and a second staple bending pocket. The anvil assembly additionally includes a length of reinforcing material extending across the first and second staple bending pockets. The width of the reinforcing material is less than the width of the first and second staple bending pockets such that the legs of a staple may be formed about the reinforcing material without penetrating it. Each of the first and second staple bending pockets are oval shaped and have a longitudinal axis formed at an angle to the longitudinal axis of the anvil member.

In one embodiment, the longitudinal axes of the first and second staple bending pockets are parallel to each other. In another embodiment, the longitudinal axes of the first and second staple bending pockets are perpendicular to the longitudinal axis of the anvil member.

In an alternative embodiment, the longitudinal axes of the first and second staple bending pockets converge toward the longitudinal axis of the anvil member. In a further alternative embodiment, the longitudinal axes of the first and second staple bending pockets diverge away from the longitudinal axis of the anvil member.

The anvil member further includes a longitudinal trough for receipt of the reinforcing material and extending across the first and second staple bending pockets. The longitudinal trough suspends the reinforcing member across the first and second staple bending pockets. The trough has an opening with a width less than the width of the reinforcing material to releasably retain the reinforcing material on the anvil member. In a specific embodiment, the reinforcing material is a wire.

There is also disclosed a fully formed surgical staple having a backspan having a longitudinal axis and a first leg extending from the backspan and a second leg extending from the backspan. Each of the first and second legs terminates in a tissue penetrating tip. The first leg includes a first portion having a longitudinal axis which defines a plane with the longitudinal axis of the backspan and a second portion which projects outward of the plane defined by the longitudinal axes of the backspan and the first portion. The second portion has a hooked shape to surround a reinforcing material. The second leg also includes a first portion extending from the backspan and lying within the plane and a second portion extending from the first portion and projecting outwardly of the plane.

In one embodiment, the second portion of the first leg and the second portion of the second leg are parallel to each other. In another embodiment, the second portion of the first leg and the second portion of the second leg are perpendicular to the longitudinal axis of the backspan.

In a further embodiment, the second portion of the first leg and the second portion of the second leg converge inwardly toward each other and are within the length of the backspan.

In a further alternative embodiment, the second portion of the first leg and the second portion of the second leg diverge away from each other and extend beyond the length of the backspan.

DESCRIPTION OF THE DRAWINGS

Various embodiments of the presently disclosed anvil assemblies and surgical staples formed therewith are disclosed herein with reference to the drawings, wherein.

DETAILED DESCRIPTION OF EMBODIMENTS

Embodiments of the presently disclosed anvil assemblies and surgical staples formed thereby will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
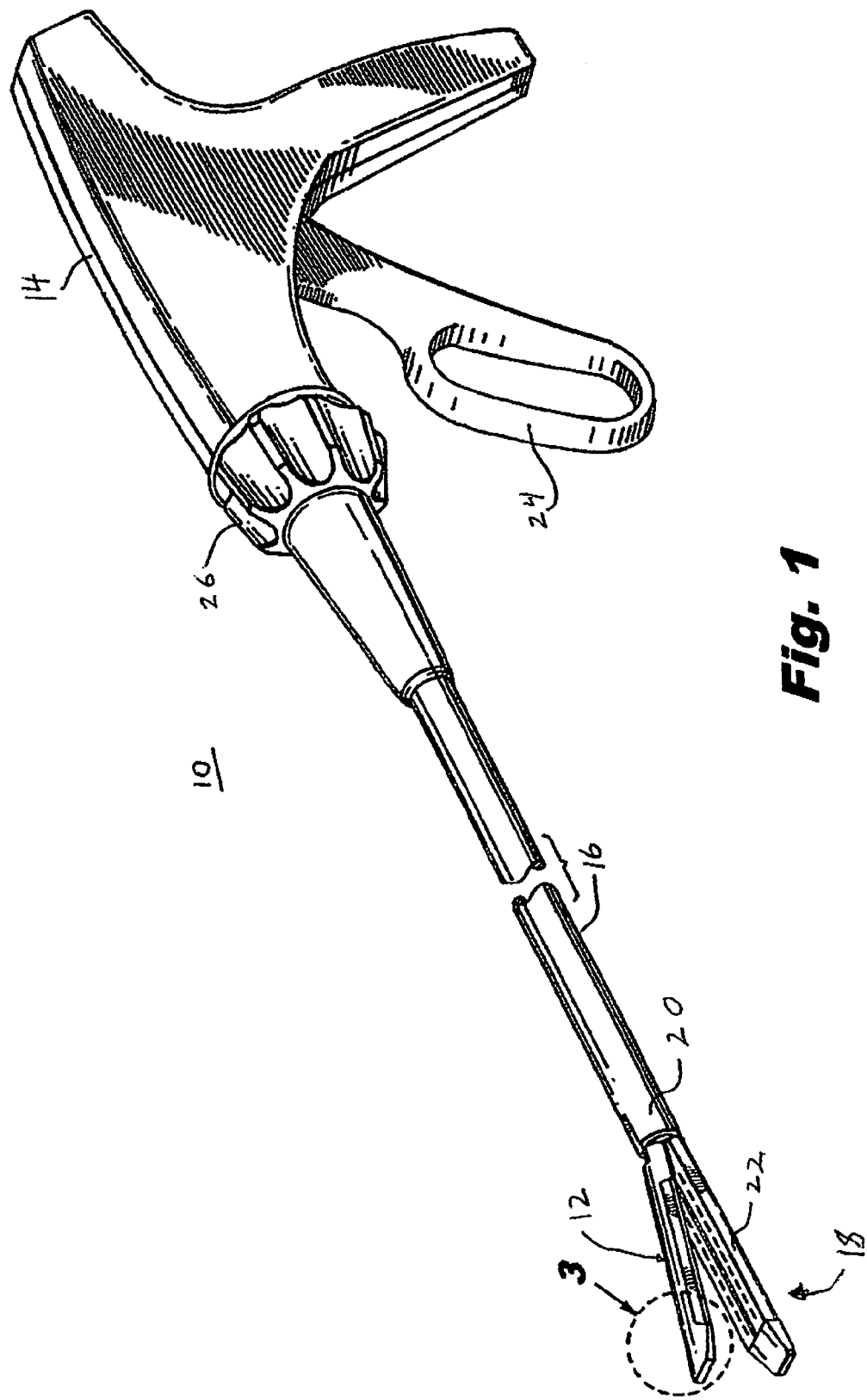
FIG. 1 is a perspective view of a surgical stapling instrument incorporating one embodiment of an anvil assembly.

Referring to FIG. 1, there is illustrated surgical stapling instrument 10 incorporating one embodiment of an anvil assembly 12. Surgical stapling instrument 10 generally includes a pistol grip style handle 14 having an elongate tubular member 16 extending distally from handle 14. An end effector 18 extends distally from a distal end 20 of elongate tubular member 16 and includes anvil assembly 12 and a staple cartridge 22. Anvil assembly 12 is movably mounted relative to staple cartridge 22. A trigger 24 is provided on handle 14 and is operable to move anvil assembly 12 from an open position spaced apart from staple cartridge 22 to a closed position bringing anvil assembly 12 into close cooperative alignment with staple cartridge 22. A rotation knob 26 is provided on handle 14 to rotate and orient end effector 18 relative to a tissue being operated upon.

Figure 2:
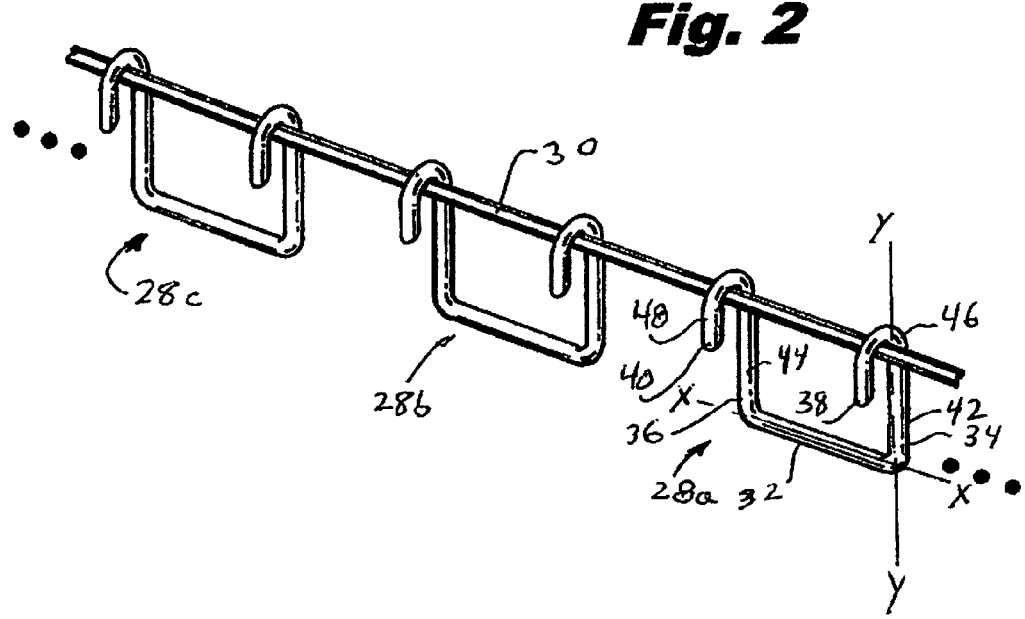
FIG. 2 is a perspective view of a series of surgical staples, formed about a reinforcing material or member, using the anvil assembly of FIG. 1.

Referring now to FIG. 2, there is disclosed a series of surgical staples 28a, 28b, 28c, etc. which have been formed over a reinforcing member or wire 30. Wire 30 is provided to ensure uniform clamping pressure along the length of a pair of tissue edges being stapled together. This is particularly advantageous where staples 28a, 28b, 28c are formed of a relatively flexible material which may be insufficient to uniformly clamp the tissues by themselves. The disclosed staples 28a, 28b, 28c, etc. and reinforcing member or wire 30 may be formed from a variety of materials. These materials may include metal materials such as, for example, stainless steel, titanium, etc. Alternatively, they may be formed from a variety of polymeric or absorbable materials. Staples 28, 28b and 28c are shown in the fully formed state after having been driven into anvil assembly 12. The following discussion of the disclosed staples will be given with regard to staple 28a.

Staple 28a generally includes a backspan 32 having first and second legs 34 and 36 extending from backspan 32 and terminating in first and second tissue penetrating tips 38 and 40. First and second legs 34 and 36 include respective first portions 42 and 44 extending from backspan 32. Second portions 46 and 48 of first and second legs 34 and 36 extend from respective first portions 42 and 44 and terminate in tissue penetrating tips 38 and 40.

In the preformed state, first and second legs 34 and 36 are generally straight. For example, first portion 42 and second portion 46 of first leg 34 are straight and lie along a common axis y-y. However, in the fully formed state, the second portions of each leg, for example, second portion 46 of first leg 34 forms a bend or a hook which lies outside of a plane defined by axis y-y of first portion 42 and a longitudinal axis x-x of backspan 32.

Figure 3:
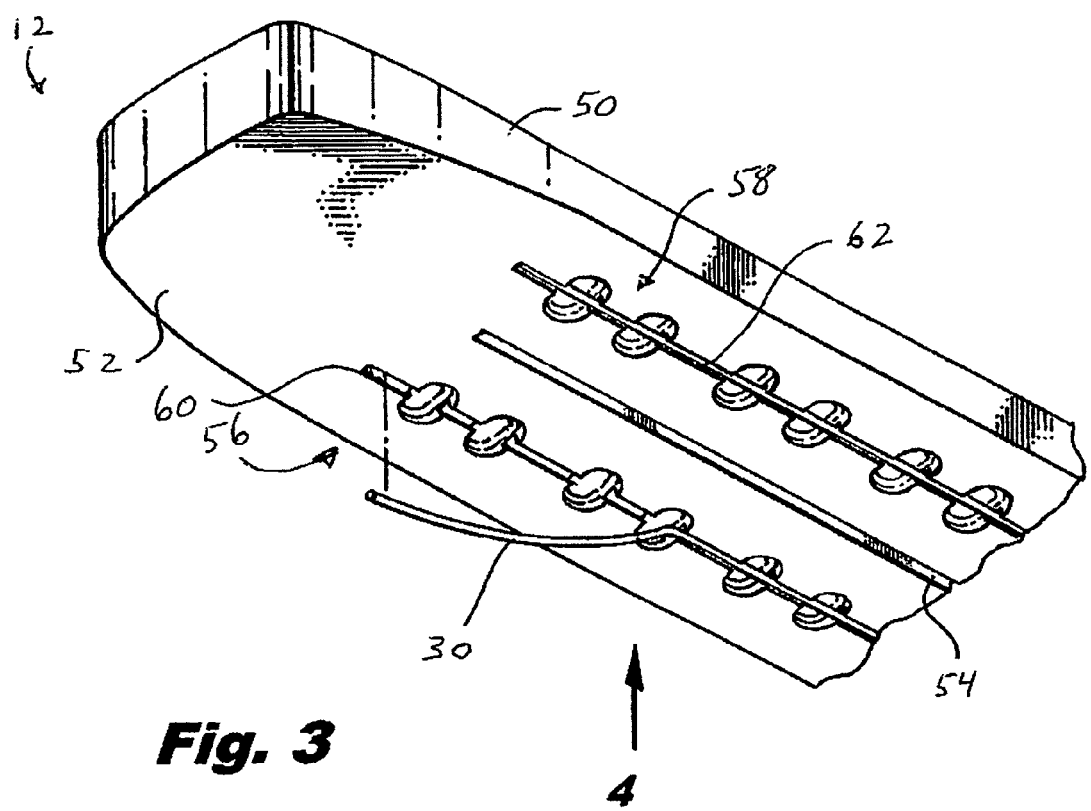
FIG. 3 is a perspective view of one embodiment of an anvil assembly including an anvil and a reinforcing member.

Referring now to FIG. 3, anvil assembly 12 generally includes reinforcing member or wire 30 and an anvil member 50 having an anvil face 52. Anvil member 50 includes a knife slot 54 extending substantially the length of the anvil member 50. Knife slot 54 is provided to sever tissues captured between anvil assembly 12 and staple cartridge 22. Rows of staple bending pockets 56 and 58 extend lengthways along anvil face 52 and on either side of knife slot 54. Rows of staple bending pockets 56 and 58 are provided to form the second portions of each leg of the disclosed staples into their bent or hooked shape as described in more detail hereinbelow.

In order to temporarily support a reinforcing member such as, for example, wire 30, on anvil face 52, a pair of longitudinal troughs or channels 60 and 62 extend longitudinally along anvil face 52 and extend across rows of staple bending pockets 56 and 58.

Figure 4:
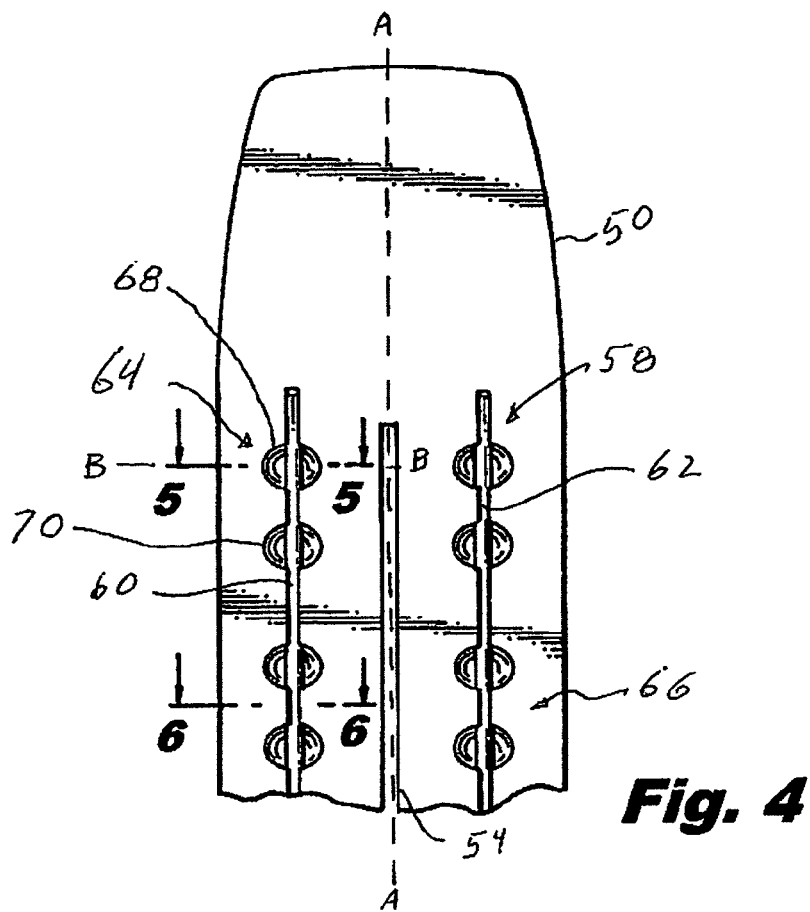
FIG. 4 is a top plan view of an anvil face of the anvil of FIG. 3.

Referring now to FIG. 4, rows of staple bending pockets 56 and 58 each include pairs of staple bending pockets 64 and 66 respectively, for forming the legs of the disclosed staples about tissue. For example, pair of staple bending pockets 64 includes a first, generally oval staple bending pocket 68 and a second, generally oval staple bending pocket 70. As noted hereinabove, second portions 46 and 48 of staple 28a are formed into a bent or hooked configuration substantially perpendicular to longitudinal axis x-x of backspan 32. In order to obtain this perpendicular orientation, anvil member 50 includes a longitudinal axis A-A and staple bending pockets 68 and 70 are oriented perpendicular to longitudinal axis A-A. Specifically, longitudinal axis B-B of oval staple bending pocket 68 is perpendicular to longitudinal axis A-A of anvil member 50.

Figure 5:
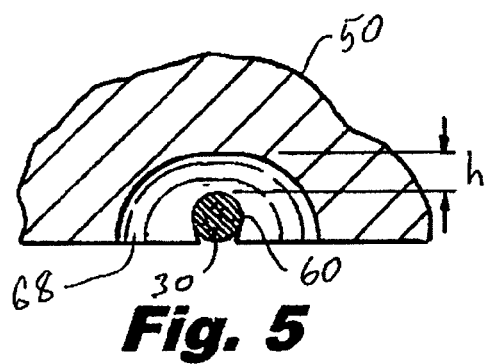
FIG. 5 is a cross sectional view taken along line 5-5 of FIG. 4.
Figure 6:
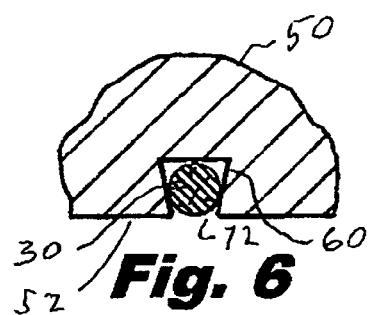
FIG. 6 is a cross sectional view taken along line 6-6 of FIG. 4.

Referring for the moment to FIGS. 5 and 6, as noted hereinabove, trough or channel 60 is provided to support wire 30 along anvil face 52 of anvil member 50 and over the rows of staple bending pockets. As best shown in FIG. 5, where wire 30 passes over a staple bending pocket such as, staple bending pocket 68, it is supported within trough 60 a sufficient height h to allow the second portion of the disclosed surgical staples to pass beneath wire 30 and allow it to be bent within staple bending pocket 68.

Referring now to FIG. 6, and as noted hereinabove, wire 30 is temporarily supported along anvil face 52 within trough 60. In order to prevent inadvertent or premature release of wire 30 from anvil member 50, trough 60 is formed with an opening 72 which is slightly less than the width of wire 30 in order to temporarily pinch or retain wire 30 within trough 60.

It should be noted that the reinforcing member can comprise a wire, suture, strand of material, strip of material, or tab of material. The reinforcing member is in certain preferred embodiments less in width than the width of the staple bending pockets. The reinforcing member can extend in length across more than one staple bending pocket.

Figure 7:
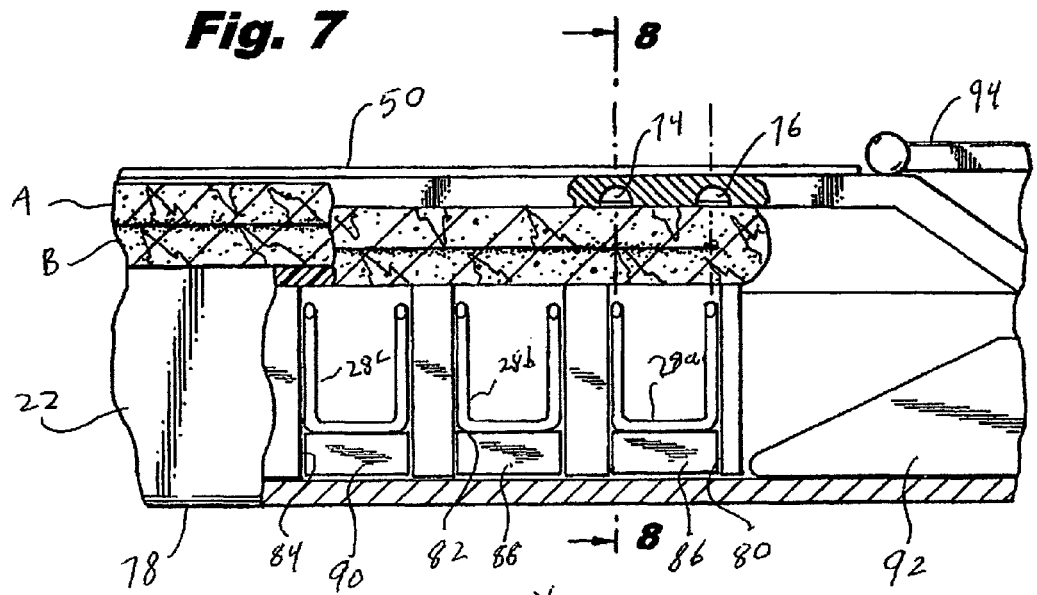
FIG. 7 is a cross sectional view of the distal end of the surgical stapling instrument of FIG. 1 positioned about tissue sections.

Referring now to FIGS. 7-10, the use of anvil assembly 12, including reinforcing wire 30, and a disclosed staple such as, for example, staple 28a to secure a pair of tissue sections together will now be described. As noted hereinabove, surgical stapling instrument 10 includes an end effector 18 extending distally from a distal end 20 of elongate member 16 which includes anvil assembly 12 and staple cartridge 22. The anvil assembly 12, discussed above with regard to FIGS. 2 through 6, and the staple cartridge 22 are movable relative to one another so that tissue can be clamped therebetween. As best shown in FIG. 7, anvil member 50 includes a pair of proximal staple bending pockets 74 and 76 which are identical to staple bending pockets 68 and 70 described hereinabove. Staple cartridge 22 generally includes a body portion 78 having a plurality of staple holding pockets such as, for example, staple holding pockets 80, 82, 84 etc. which are provided to retain surgical staples 28a, 28b, 28c etc. Pushers 86, 88, 90 etc. are provided within staple holding pockets 80, 82 and 84, respectively, to support the surgical staples contained therein. A handle is at the proximal end of the elongate member 16. A drive bar 91 (FIG. 9) is operatively associated with trigger 24 on surgical stapling instrument 10 (FIG. 1) for translating the drive bar 91 through the staple cartridge. A sled 92 is positioned adjacent the drive bar 91. Drive bar 91 and sled 92 are provided to drive the disclosed surgical staples such as, surgical staple 28a out of staple pocket 80 and toward staple bending pockets 74 and 76 in anvil member 50. In certain embodiments, the sled has ramped or wedge-shaped surfaces for interacting with staple pushers. As the drive bar is translated through the staple cartridge, the sled is translated in the same direction, pushing the staple pushers, and the staple pushers drive the staples out of the body portion 78 against the anvil member. The sled and pushers disclosed in U.S. Pat. No. 5,762,256 and U.S. Pat. No. 5,865,361, the entire disclosures of which are hereby incorporated by reference herein, can be used.

Figure 8:
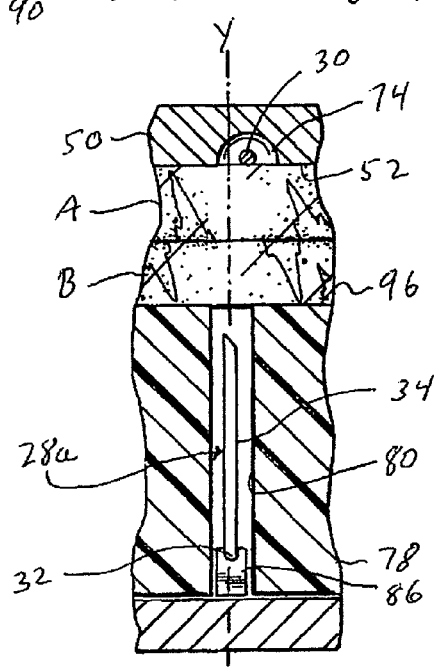
FIG. 8 is a cross sectional view taken along line 8-8 of FIG. 7.

With reference to FIGS. 7 and 8, in the initial position, the longitudinal axes of the legs of these disclosed surgical staples are offset relative to wire 30 which is suspended through the staple bending pockets. Specifically, for example, longitudinal axis y-y of first leg 34 of staple 28a is offset relative to the center of staple bending pocket 74 (FIG. 8). This allows first leg 34 to enter staple bending pocket 74 and pass around wire 30 during formation. While only staple bending pocket 74 is illustrated as being offset relative to first leg 34, it should be understood that all the staple bending pockets in anvil member 50 are offset relative to the staple legs to be formed therein so as to allow all staple legs to enter the staple bending pockets and pass around wire 30.

As shown in FIGS. 7 and 8, initially anvil member 50 is moved to the closed position relative to staple cartridge 22 by a clamping bar 94 to thereby capture a pair of tissue sections such as, for example, for tissue section A and tissue section B between anvil face 52 of anvil member 50 and in the cartridge face 96 of staple cartridge 22.

Figure 9:
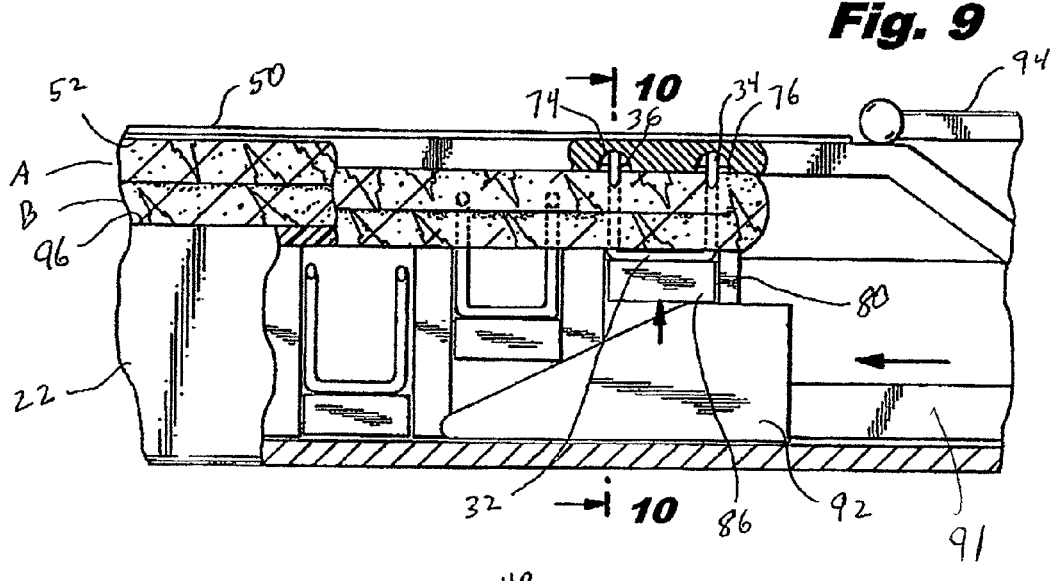
FIG. 9 is a cross sectional view similar to FIG. 7 illustrating a series of surgical staples being driven through tissue and into the anvil.
Figure 10:
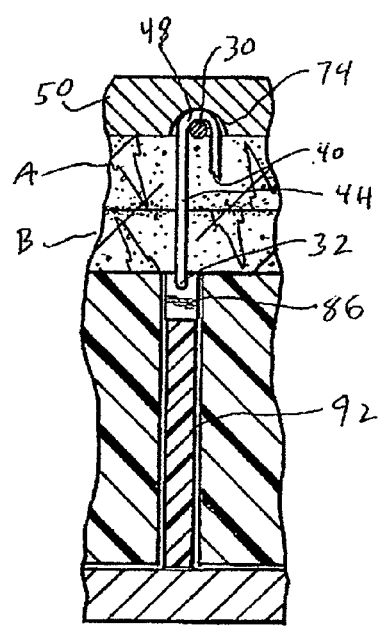
FIG. 10 is a cross sectional view, taken along line 10-10 of FIG. 9, illustrating a tissue penetrating end of one of the surgical staples formed about the reinforcing member.

Referring now to FIGS. 9 and 10, once anvil member 50 has been moved to the closed position relative to staple cartridge 22, trigger 24 of surgical stapling instrument 10 (FIG. 1) is activated to drive drive bar 92 distally within staple cartridge 22. As drive bar 92 moves distally, drive bar 92 engages and moves pusher 86 upwardly within staple holding pocket 80 to thereby drive first and second legs 34 and 36 into staple bending pockets 74 and 76.

With specific reference to FIG. 10, as the legs are driven toward their respective staple bending pockets such as, for example, as second leg 36 is driven toward staple bending pocket 74, tissue penetrating tip 40 passes into staple bending pocket 74 and around wire 30 to thereby form second portion 48 of second leg 36 into a bent or hooked configuration about wire 30. This unique method of forming a leg of the surgical staple allows the additional material of second section 48, proximal to tissue penetrating tip 40, to again penetrate into tissue section A to further secure surgical staple 28a through tissue sections A and B.

Figure 11:
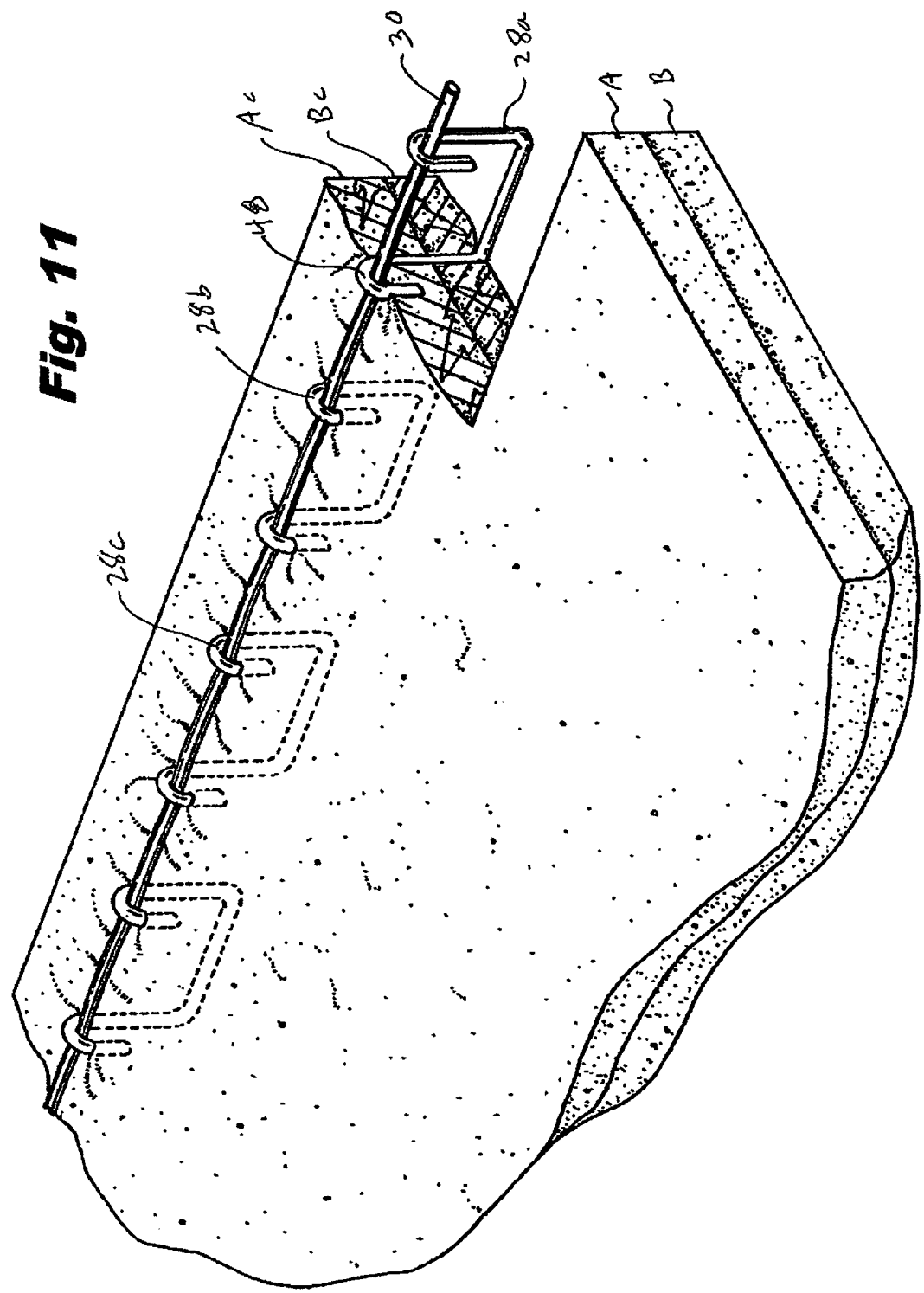
FIG. 11 is a perspective view of a pair of tissue sections secured together by a series of staples formed about a reinforcing member.

As best shown in FIG. 11, tissue sections A and B are secured together by surgical staples 28a, 28b, 28c, etc. and the clamping of tissue sections A and B is further reinforced by the presence of wire 30 secured to the surface of tissue section A by the bent respective surgical staples. It should be further noted, in this particular configuration, the bent or hooked portions such as, for example, second portion 48 of surgical staple 28a faces away from the cut edges Ac and Bc formed by a knife blade (not shown) passing through knife slot 54 in anvil member 50.

Figure 12:
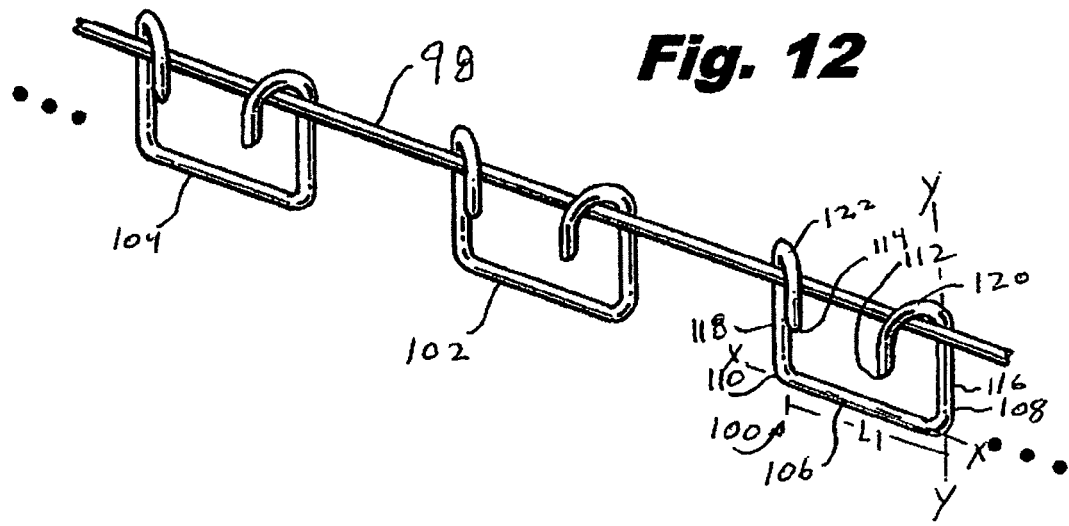
FIG. 12 is a perspective view of another series of surgical staples formed over a reinforcing member.

Referring now to FIG. 12, there is disclosed another embodiment of a reinforcing member or wire 98 having a plurality of surgical staples 100, 102 and 104 formed about wire 98. Surgical staple 100, in the formed condition, is identical to surgical staples 102 and 104 in their formed conditions and generally includes a backspan 106 having a first leg 108 and a second leg 110 extending from backspan 16. First and second legs 108 and 110 terminate in respective tissue penetrating tips 112 and 114. First leg 108 includes a first portion 116 and second leg 110 includes a first portion 118. First leg 108 includes a second portion 120 and second leg 110 includes a second portion 122.

As shown, backspan 106 has a longitudinal axis x-x and first portion 116 of first leg 108 has a longitudinal axis y-y which is perpendicular to longitudinal axis x-x of backspan 106 to define a plane. First portion 118 of second leg 110 is also perpendicular to backspan 106 and lies within the same plane. As shown, second portions 120 and 122 of first leg 108 and second leg 110, respectively, extend outwardly from the plane defined by backspan 106 and first portions 116 and 118. In this particular embodiment, second portions 120 and 122 angle inwardly toward backspan 106 and are formed within length L1 of backspan 106.

Figure 13:
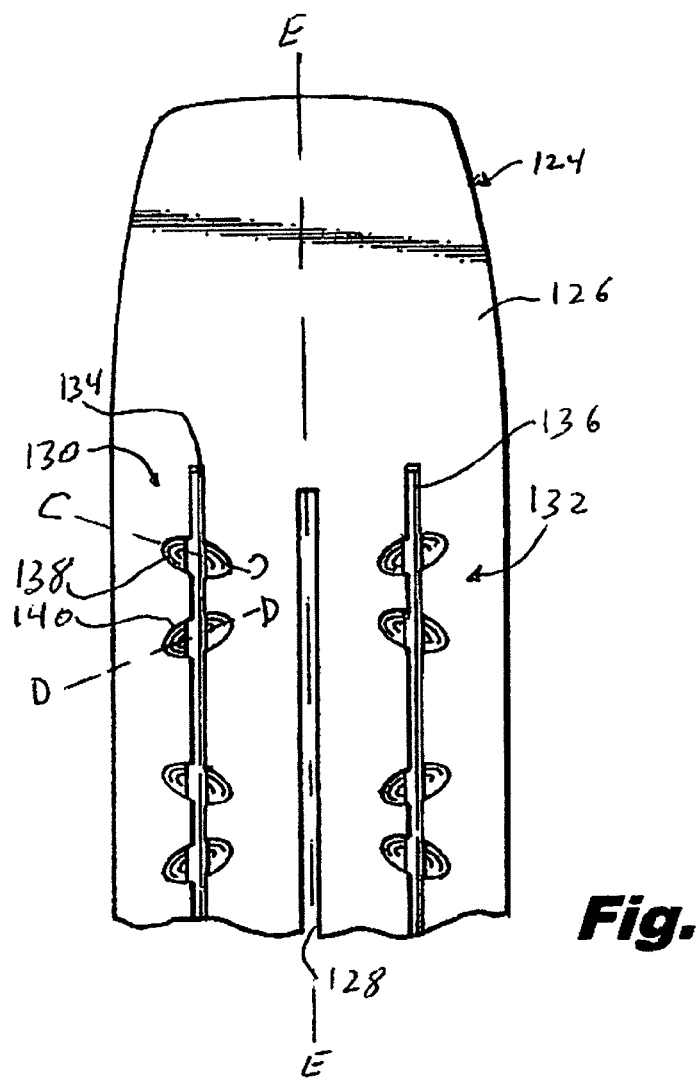
FIG. 13 is a top plan view of an alternative embodiment of an anvil used to form the staples of FIG. 12.

Referring now to FIG. 13, in order to form surgical staple 100 into the disclosed configuration, there is provided an alternative embodiment of an anvil member 124 having an anvil face 126. The anvil member 124 forms part of a surgical stapling instrument, as discussed above in connection with FIGS. 1 and 7 through 10. Anvil member 124 includes a knife slot 128 and rows of staple bending pockets 130 and 132 formed in anvil face on either side of knife slot 128. Similar to anvil member 50 described hereinabove, anvil member 124 includes a pair of channels 134 and 136 extending across anvil face 126 and across rows of staple bending pockets 130 and 132. Channels 134 and 136 are provided to retain a reinforcing member or wire 98 in a manner substantially described hereinabove with regard to wire 30.

In order to form second portions 120 and 122 into their respective bent configurations directed inwardly towards backspan 106, row of staple bending pockets 130 includes a first staple bending pocket 138 and a second staple bending pocket 140. As shown, first staple bending pocket 138 has an axis C-C and second staple bending pocket 140 has an axis D-D both of which are oriented at an angle which converges toward knife slot 128 and is at an angle other than 90° with respect to longitudinal axis E-E of anvil member 124. It should be noted that, unlike the previous embodiment, staple bending pockets 138 and 140 angle inwardly toward knife slot 128 such that, upon formation, bent second portions 120 and 122 of surgical staple 100 angle inwardly and face edges of tissue cut by a knife blade (not shown) passing through knife slot 128.

Figure 14:
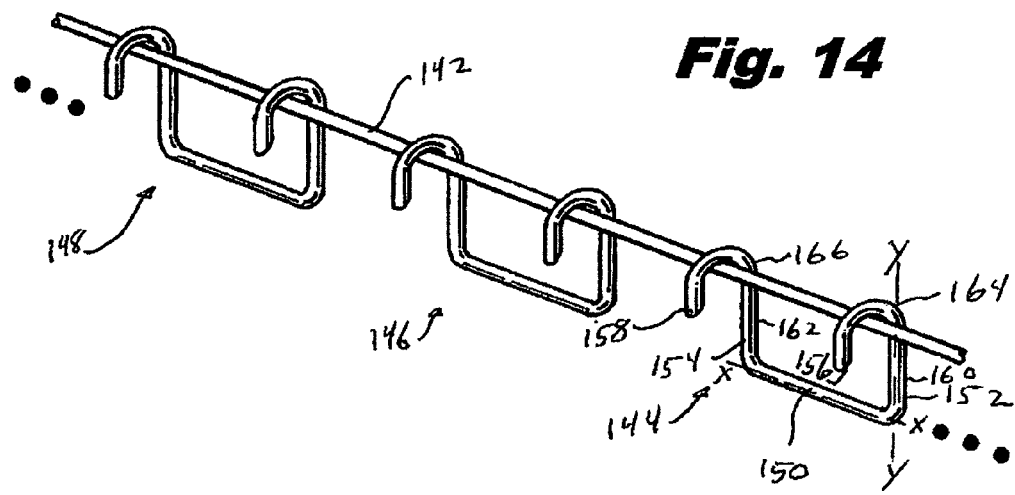
FIG. 14 is a perspective view of a further series of surgical staples formed over a reinforcing member.

With reference to FIG. 14, there is disclosed another embodiment of a reinforcing member or wire 142 having a plurality of staples 144, 146 and 148 formed about wire 142. As with prior series of staples, surgical staple 144, in the formed condition, is identical to surgical staples 146 and 148 and generally includes a backspan 150 having a first leg 152 and a second leg 154 extending from backspan 150 and terminating in respective tissue penetrating tips 156 and 158. First leg 152 includes a first portion 160 and second leg 154 includes a first portion 162. Similar to prior embodiments, first leg 152 includes a second portion 164 and second leg 154 includes a second portion 166.

Backspan 150 has a longitudinal axis x-x and first portion 160 of first leg 152 has a longitudinal axis y-y which is perpendicular to longitudinal axis x-x of backspan 150 to define a plane. First portion 162 of second leg 154 is also perpendicular to backspan 150 and lies within the plane. As shown, second portions 164 and 166 of first leg 152 and second leg 154, respectively, extend outward of the plane defined by backspan 150 and first portions 160 and 162. In this particular embodiment, second portions 164 and 166 are parallel to each other and form an angle other than 90° with respect to longitudinal axis x-x of backspan 150.

Figure 15:
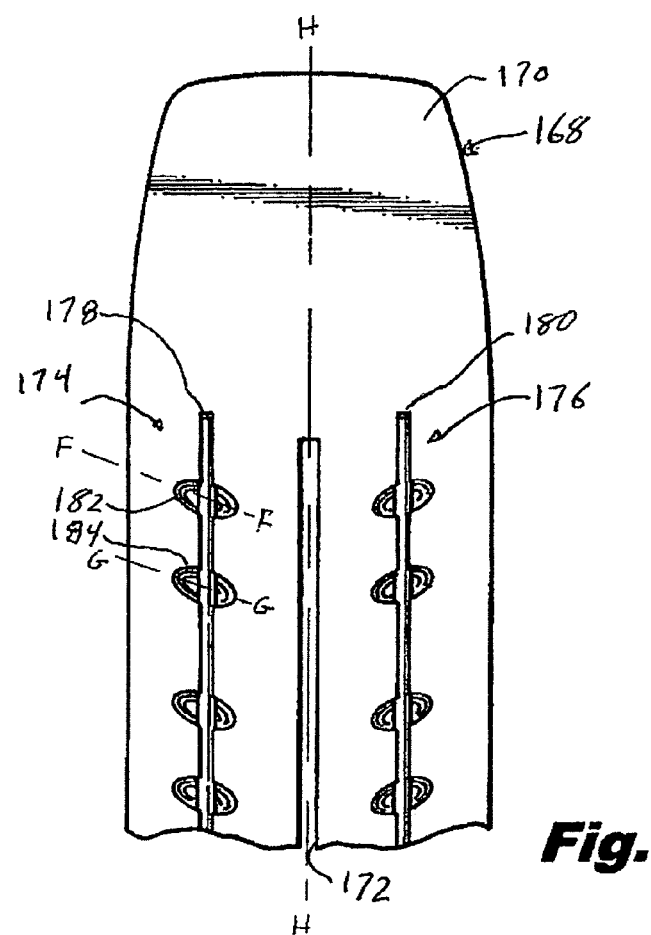
FIG. 15 is a top plan view of a further alternative embodiment of an anvil used to form the staples of FIG. 14.

Referring to FIG. 15, in order to form surgical staple 144 into the disclosed configuration, there's provided a further alternative embodiment of an anvil member 168 having an anvil face 170. The anvil member 168 forms part of a surgical stapling instrument, as discussed above in connection with FIGS. 1 and 7 through 10. Anvil member 168 includes a knife slot 172 extending substantially the length of anvil member 168 and rows of staple bending pockets 174 and 176 formed on either side of knife slot 172. Anvil member 168 additionally includes channels 178 and 180 extending across anvil face 170 and across rows of staple bending pockets 174 and 176 to temporarily secure wire 142 in a manner described hereinabove with regard to wire 30.

In order to form second portions 164 and 162 into their angled and parallel bent configurations with respect to backspan 150, row of staple bending pockets 174 includes a first staple bending pocket 182 and a second staple bending pocket 184. First staple bending pocket 182 has a longitudinal axis F-F which is parallel to a longitudinal axis G-G of second staple bending pocket 184. Both first and second staple bending pockets 182 and 184 form an angle with respect to a longitudinal axis H-H of anvil member 168.

Figure 16:
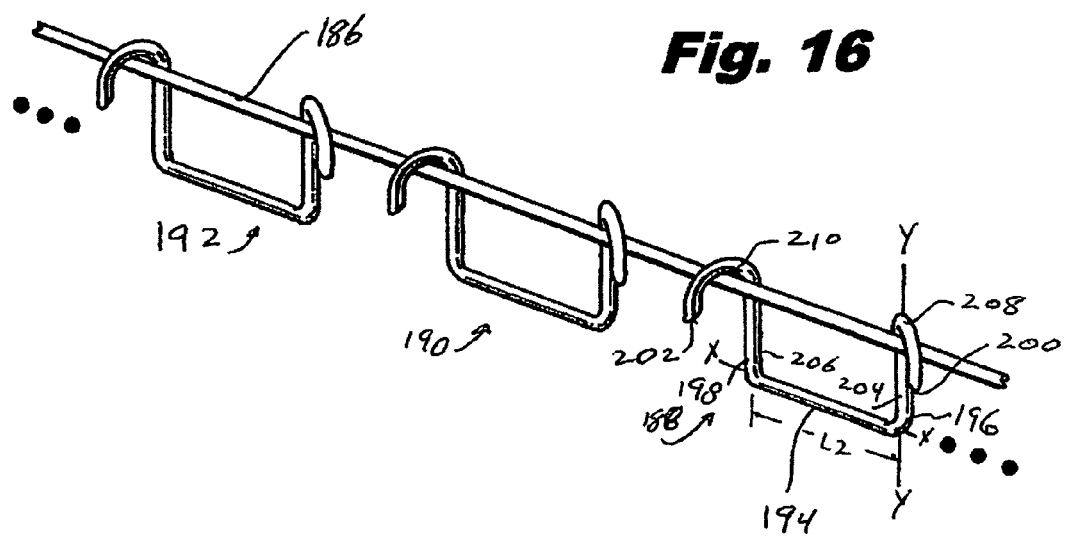
FIG. 16 is a perspective view of still another series of surgical staples formed over a reinforcing member.

Referring now to FIG. 16, there is disclosed a further embodiment of a reinforcing member or wire 186 having surgical staples 188, 190 and 192 formed about reinforcing wire 186. Surgical staple 188 is identical to surgical staples 190 and 192 and generally includes a backspan 194 having a first leg 196 and a second leg 198 extending from backspan 194. Tissue penetrating tips 200 and 202 are formed on first and second legs 196 and 198, respectively. First and second legs 196 and 198 include respective first portions 204 and 206 and respective second portions 208 and 210. First portion 204 of first leg 196 has a longitudinal axis y-y which is perpendicular to a longitudinal axis x-x of backspan 194 and defines a plane there between. As with previous embodiments, in the formed condition, second portions 208 and 210 extend beyond the plane defined by first portion 204 and backspan 194.

In this particular embodiment, second portions 208 and 210 are angled or splayed outwardly relative to backspan 194 such that they extend beyond a length L2 of backspan 194.

Figure 17:
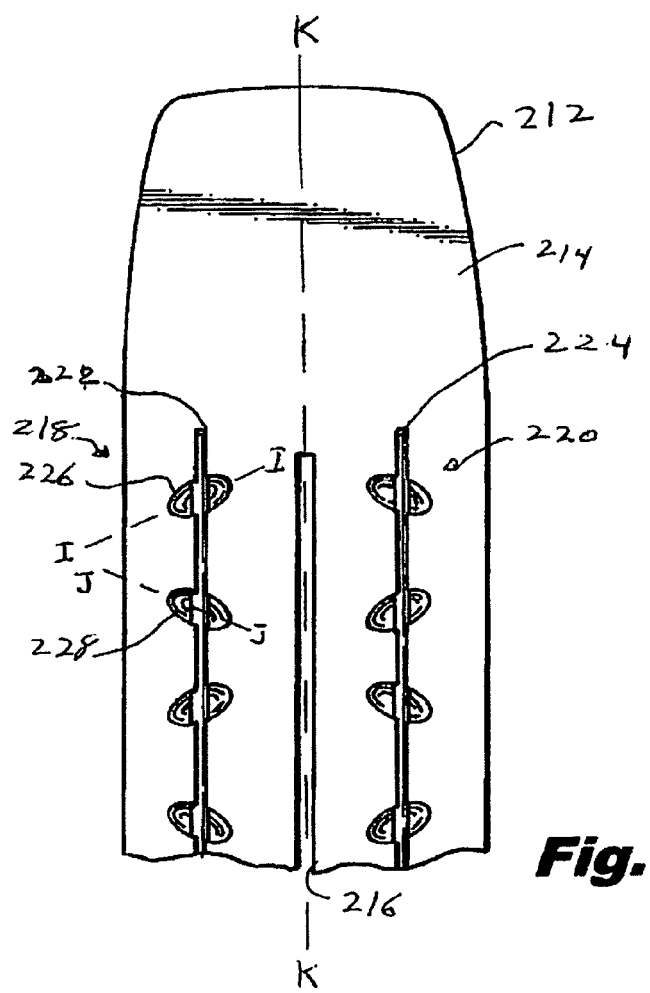
FIG. 17 is a top plan view of another alternative embodiment of an anvil used to form the staples of FIG. 16.

In order to form surgical staples 188, 190 and 192 into their disclosed configurations, there is provided an anvil member 212 (FIG. 17) having an anvil face 214. The anvil member 212 forms part of a surgical stapling instrument, as discussed above in connection with FIGS. 1 and 7 through 10. Anvil member 212 includes a longitudinally extending knife slot 216 and rows of staple bending pockets 218 and 220 formed in anvil face 214 on either side of knife slot 216. A pair of channels 222 and 224 is provided across anvil face 214 and through rows of staple bending pockets 218 and 220 to hold wire 186.

Row of staple bending pockets 218 includes a first staple bending pocket 226 and a second staple bending pocket 228. First staple bending pocket 226 has a longitudinal axis I-I and second staple bending pocket 228 has a longitudinal axis J-J both of which are oriented at an angle which converges away from knife slot 216 and is at an angle other than 90° with respect to a longitudinal axis K-K of anvil member 212.

Figure 18:
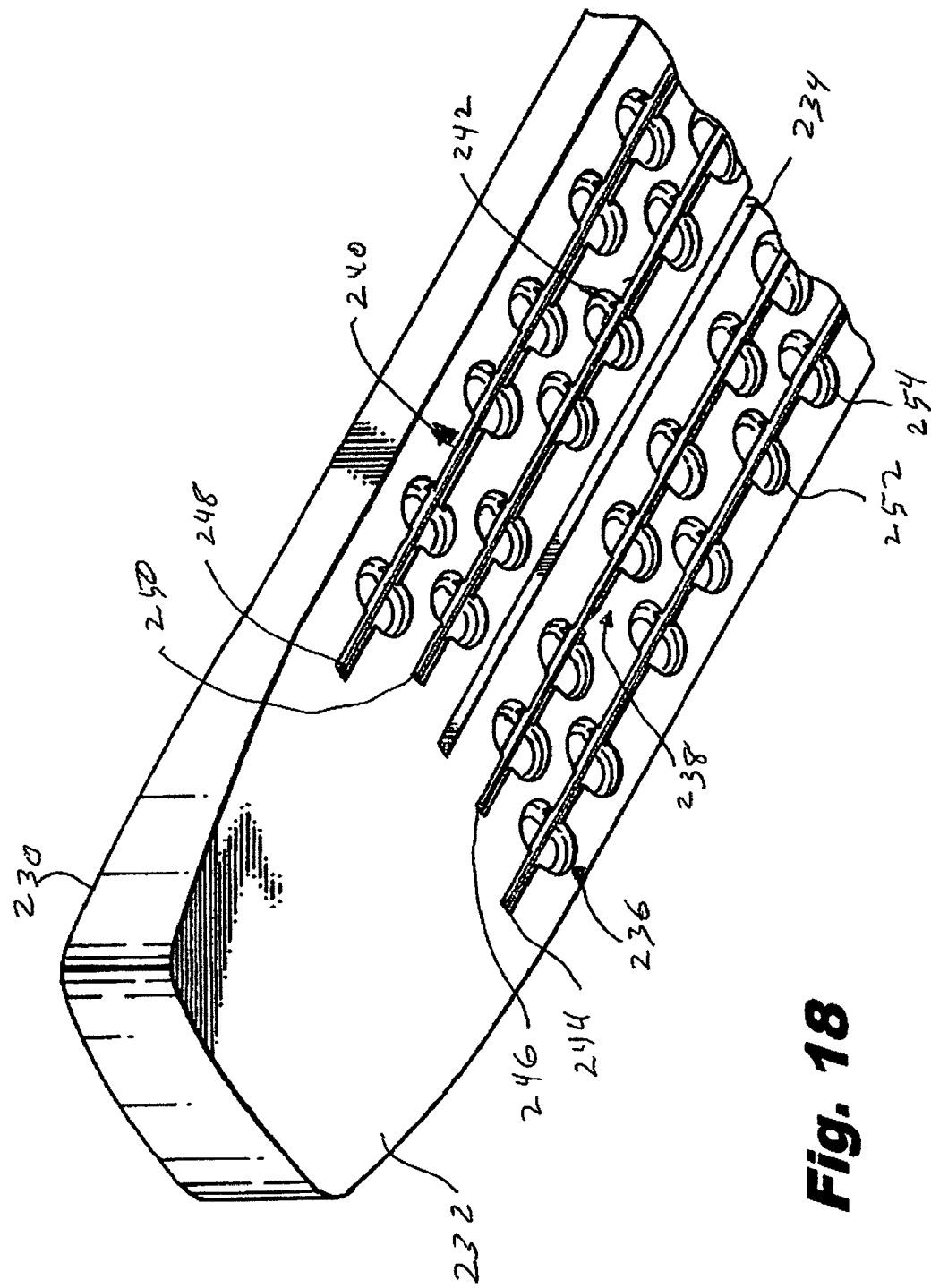
FIG. 18 is a top plan view of a further alternative embodiment of an anvil used to form multiple rows of surgical staples about reinforcing members.

With reference to FIG. 18, there is disclosed a further alternative embodiment of an anvil member 230 suitable for use in forming the disclosed surgical staples about reinforcing member or wire. The anvil member 230 forms part of a surgical stapling instrument, as discussed above in connection with FIGS. 1 and 7 through 10. Anvil member 230 includes an anvil face 232 having a knife slot 234 extending longitudinally through anvil member 230. Rows of staple bending pockets 236, 238, 240 and 242 are provided alongside knife slot 234. As with the prior anvil embodiments, longitudinally extending channels 244, 246, 248 and 250 extend through rows of staple bending pockets 236, 238, 240 and 242 to removably support lengths of reinforcing member across the staple pockets such as, for example, staple pockets 252 and 254. It should be noted that in this, as well as in prior, alternative embodiments of the disclosed anvil members, staple pockets 252 and 254 may assume any of the configurations and orientations previously disclosed. For example, all the staple pockets 252 and 254 in anvil member 230 may be oriented in the same or in differing directions.

It is contemplated that the fastener assembly having one or more reinforcing members and staples as discussed above in connection with FIGS. 2 through 6 and 11 through 18 can be used in surgical stapling instruments that have circular or arcuate anvils, and/or surgical stapling instruments in which the staples are driven against the anvil in the same direction as the anvil (or cartridge) moves to clamp tissue.

It will be understood that various modifications may be made to the embodiments disclosed herein. For example, the disclosed staple bending pockets may assume shapes other than oval such as, for example, circular, FIG. 8, etc. Further, as noted hereinabove, the disclosed reinforcing members may include materials other than wire such as for example thin strips of webbing material, flat ribbons of metallic or polymeric materials, etc. so long as the links of reinforcing material do not completely occlude the disclosed staple bending pockets. Therefore, the above description should not be construed as limiting, but merely as exemplifications of particular embodiments. Those skilled in the art will envision other modifications within the scope and spirit of the claims appended hereto.

The invention claimed is:

1. An anvil assembly for use with a surgical stapling instrument comprising;
   an anvil member having a longitudinal axis and a first staple bending pocket and a second staple bending pocket; and
   a length of reinforcing member extending across the first and second staple bending pockets, wherein the width of the reinforcing member is less than the width of the first and second staple bending pockets.

2. The anvil assembly as recited in claim 1, wherein each of the first and second staple bending pockets are oval shaped and have a longitudinal axis formed at an angle to the longitudinal axis of the anvil member.

3. The anvil assembly as recited in claim 2, wherein the longitudinal axes of the first and second staple bending pockets are parallel to each other.

4. The anvil assembly as recited in claim 2, wherein the longitudinal axes of the first and second staple bending pockets are perpendicular to the longitudinal axis of the anvil member.

5. The anvil assembly as recited in claim 2, wherein the longitudinal axes of the first and second staple bending pockets converge toward the longitudinal axis of the anvil member.

6. The anvil assembly as recited in claim 2, wherein the longitudinal axes of the first and second staple bending pockets diverge away from the longitudinal axis of the anvil member.

7. The anvil assembly as recited in claim 1, wherein the anvil member includes a longitudinal trough for receipt of the reinforcing member and extending across the first and second staple bending pockets.

8. The anvil assembly as recited in claim 7, wherein the trough has an opening with a width less than the width of the reinforcing member.

9. The anvil assembly as recited in claim 7, wherein the longitudinal trough suspends the reinforcing member across the first and second staple bending pockets.

10. A surgical stapling instrument, comprising:
    an elongate member;
    a handle assembly at a proximal end of the elongate member; and
    an end effector at a distal end of the elongate member, the end effector including:
    an anvil assembly including:
       an anvil member having a longitudinal axis and a first staple bending pocket and a second staple bending pocket; and
       a length of reinforcing member extending across the first and second staple bending pockets, wherein the width of the reinforcing member is less than the width of the first and second staple bending pockets; and
    a staple cartridge, the anvil assembly and staple cartridge being movable relative to one another.

11. The surgical stapling instrument as recited in claim 10, wherein the anvil member includes a longitudinal trough for receipt of the reinforcing member.

12. The surgical stapling instrument as recited in claim 11 wherein the longitudinal trough extends across the first and second staple bending pockets.

13. The surgical stapling instrument as recited in claim 11, wherein the trough has an opening with a width less than the width of the reinforcing member.

14. The surgical stapling instrument as recited in claim 11, wherein the longitudinal trough suspends the reinforcing member across the first and second staple bending pockets.

15. The surgical stapling instrument as recited in claim 10, wherein the staple cartridge has a body portion with a plurality of staple holding pockets.

16. The surgical stapling instrument as recited in claim 15, wherein the staple holding pockets each contain a staple.

17. The surgical stapling instrument as recited in claim 15, wherein the staple cartridge has a sled.

18. The surgical stapling instrument as recited in claim 10, further comprising a drive bar operatively associated with the handle assembly.

19. The surgical stapling instrument as recited in claim 18, wherein the handle assembly includes a trigger.

20. The surgical stapling instrument as recited in claim 10, wherein the reinforcing member is selected from the group consisting of a wire, suture, or strip of material.

21. The surgical stapling instrument as recited in claim 10, wherein the length of reinforcing member extends across more than two staple bending pockets.

22. The surgical stapling instrument as recited in claim 10, wherein the anvil member is selected from the group consisting of a circular anvil member and an arcuate anvil member.

* * * * *